United States Patent [19]

Kletschka

[11] Patent Number: 4,895,493
[45] Date of Patent: Jan. 23, 1990

[54] ROTARY PUMP

[76] Inventor: Harold D. Kletschka, 1925 Noble Dr., Minneapolis, Minn. 55422

[21] Appl. No.: 217,653

[22] Filed: Aug. 18, 1988

Related U.S. Application Data

[62] Division of Ser. No. 62,137, Jun. 12, 1987, Pat. No. 4,844,707.

[51] Int. Cl.⁴ .......................................... F04B 39/14
[52] U.S. Cl. ................................ 417/238; 417/316; 417/319; 417/420; 417/423.14
[58] Field of Search ............... 417/238, 316, 319, 360, 417/374, 407, 420, 423.8, 423.11, 423.12, 423.13, 423.14, 572, 423.5; 184/6.4, 6.11, 6.24; 415/90, DIG. 4

[56] References Cited

U.S. PATENT DOCUMENTS

| Re. 28,742 | 3/1976 | Rafferty et al. . | |
|---|---|---|---|
| 3,185,873 | 5/1965 | Rosenfeld | 417/374 |
| 3,306,221 | 2/1967 | Goodpasture . | |
| 3,321,081 | 5/1967 | Willinger . | |
| 3,420,184 | 3/1969 | Englesberg et al. | 417/420 |
| 3,465,681 | 9/1969 | Zimmerman . | |
| 3,487,784 | 1/1970 | Rafferty et al. . | |
| 3,575,536 | 4/1971 | Jacobs et al. . | |
| 3,647,324 | 3/1972 | Rafferty et al. . | |
| 3,864,055 | 2/1975 | Kletschka et al. . | |
| 3,889,489 | 6/1975 | Casey et al. . | |
| 3,932,068 | 1/1976 | Zimmerman . | |
| 4,037,984 | 7/1977 | Rafferty et al. . | |
| 4,044,567 | 8/1977 | Dix et al. . | |
| 4,047,847 | 9/1977 | Oikawa | 417/420 |
| 4,065,234 | 12/1977 | Yoshiyuka et al. | 417/420 |
| 4,120,618 | 10/1978 | Klaus . | |
| 4,120,618 | 10/1978 | Klaus | 417/420 |
| 4,135,253 | 5/1979 | Reich et al. . | |
| 4,165,206 | 8/1979 | Martin et al. . | |
| 4,562,518 | 7/1985 | Wiernicki . | |
| 4,613,289 | 9/1986 | Kotera | 417/420 |
| 4,615,413 | 10/1986 | Stevenson | 184/6.24 X |

OTHER PUBLICATIONS

Rafferty, et al., Minnesota Medicine 51:11–16 Jun. 1968.
Rafferty, et al., Minnesota Medicine 51:191–193 May (1968).
Kletschka, et al., Minnesota Medicine 58:757–781 Aug. (1975).

*Primary Examiner*—Carlton R. Croyle
*Assistant Examiner*—Eugene L. Szczecina
*Attorney, Agent, or Firm*—Dorsey & Whitney

[57] ABSTRACT

A rotary pump mechanism is disclosed which comprises a coupling section that couples an impeller and drives the coupling section and, in turn, the impeller. The coupling section incorporates most of the components of the pump that wear out and are expensive. As a result, the impeller can be disposed of without disposing of other components. The coupling section can also be changed for continuous operation of a single impeller. Although the preferred application of the invention is in the area of pumping blood and other biological fluids, the disclosed invention has utility in any application where it is desirable to turn an "impeller-like" element.

14 Claims, 5 Drawing Sheets

Fig. 6
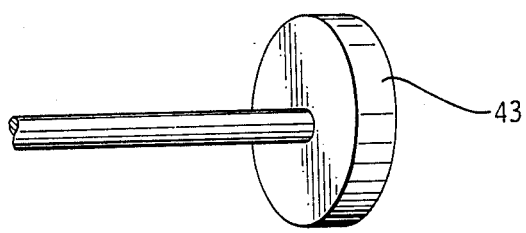
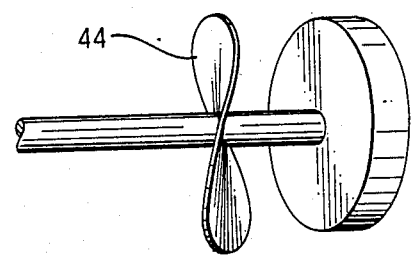
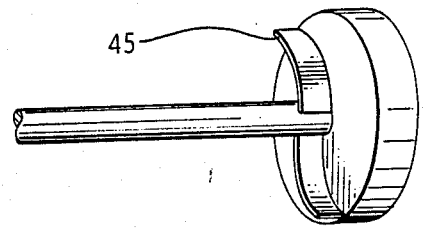
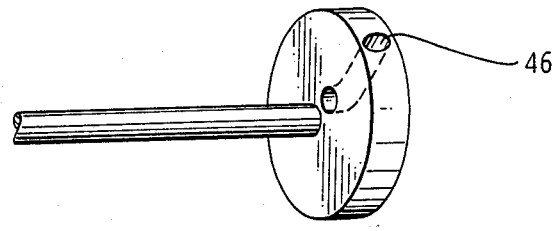

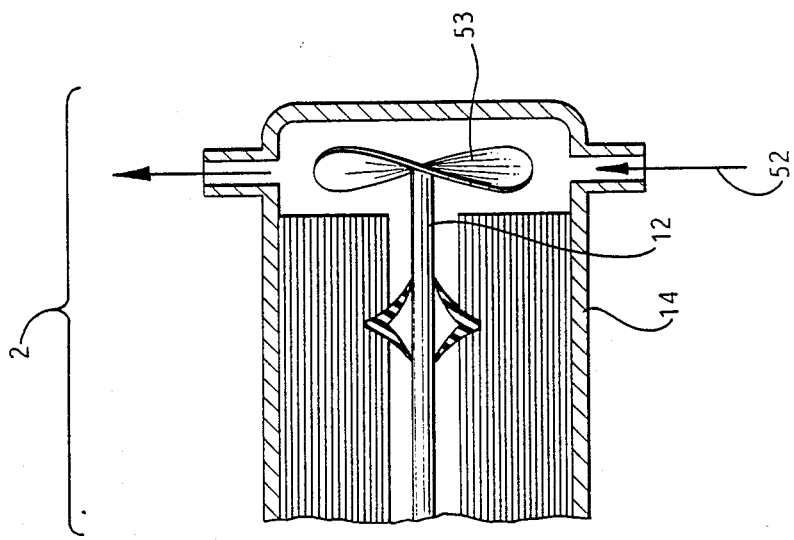
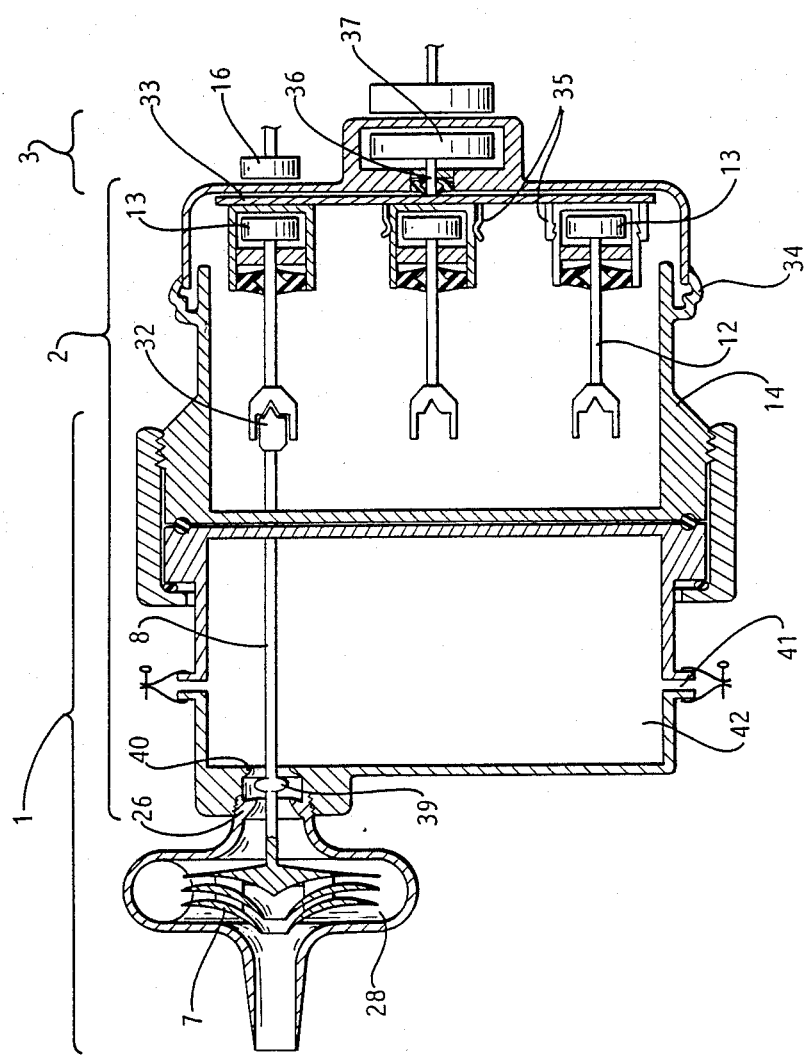

ROTARY PUMP

This is division of application Ser. No. 07/062,137, filed June 12, 1987, now U.S. Pat. No. 4,844,707.

BACKGROUND OF THE INVENTION

This invention relates to a new and improved rotary pump for use in many diverse pumping applications, especially in any situation where it would be advantageous to be able to replace or dispose of certain components of the pumping mechanism that have expended their useful lives without having to also dispose of other parts that have additional useful life and/or are more expensive to replace. These concerns are especially relevant in applications employing magnets, which are relatively expensive, as the means of driving the rotation of the pump.

The art is replete with examples of rotary pump mechanisms employing various means for driving the rotation of the pump, including but not limited to magnets, gears, electrical conduction and induction, belts and rollers. Pumps employing magnetic driving systems are exemplified by U.S. Pat. Nos. 3,647,324 and 4,037,984 of which Applicant is an inventor. These references disclose pumps for use with biological fluids, especially blood. These pumps are especially useful in heart-lung machines and devices for assisting ailing heart muscles. The pumps are comprised of a housing in which an impeller and a magnet are incorporated. The magnet is magnetically connected to a second magnet outside of the housing. The second magnet is in turn connected to a motor. When the motor rotates the second magnet, the first magnet also rotates, turning the impeller with it.

Other pumps incorporating similar magnetic driving mechanisms are represented by U.S. Pat. Nos. 3,306,221, 3,321,081, 3,575,536, 4,135,253 and 4,165,206.

These magnetic systems keep the pumped fluid separated from the mechanical driving elements of the pump, for example the motor. This feature provides the advantages of (1) preventing fluids from contacting the driving mechanism, thus preventing corrosion, electrical shorts, seizing and other undesirable results that render the driving mechanism useless; (2) preventing lubricants, detritus and other foreign material from contacting the fluid being pumped, especially when the fluid is blood; and (3) preventing the fluid being pumped from contacting air, especially when the fluid is blood.

To maintain separation between the fluid and the driving mechanism, many devices in the prior art incorporate an expensive driving mechanism, for example magnet-driven shafts or other rotatably components, into the impeller section of the pumping device. Since components associated with rotation are usually the mechanical elements that wear out most quickly, replacement of these components means replacement of the entire impeller section including components in that section which may not have outlived their useful lives. Alternatively, in some applications, especially those in the medical field where the pump is used in contact with bodily fluid or preparations of body tissues, it may be necessary to dispose of the impeller section of a pump because it cannot be reused due to the possibility of contamination or other undesirable reaction between substances from one patient and those of another. With pumps of the prior art, if the impeller and other elements contacting the biological fluid must be discarded, other components, including parts of the magnetic or other driving mechanism, must be unnecessarily discarded with the impeller. The unnecessary, inefficient and uneconomical loss of components that would still be useful is a problem that is common to many rotary pumping devices in the prior art.

It would be desirable, therefore, to provide a rotary pump that keeps fluid away from the driving mechanism, yet allows replacement or disposal of components of the pump which cannot be reused or continue to be used, without also disposing of components that are still useful.

SUMMARY OF THE INVENTION

In accordance with the instant invention, a rotary pump is disclosed which is comprised of a coupling section, including a coupling housing and a rotational member situated therein; and impeller section, including an impeller; and drive means for rotating said rotational member by action of a force between the drive means and the rotational member.

In a preferred embodiment, the rotational member comprises a shaft connected to a first magnet. The shaft is releasably joined to the impeller such that rotation of the shaft rotates the impeller. Preferably, the drive means is a second magnet which is magnetically connected to the first magnet such that rotation of the second magnet causes rotation of the first magnet and, therefore, rotation of the shaft and impeller.

In an alternative embodiment, the first magnet can be replaced by a second impeller and the drive means is a fluid pressure source (e.g., a stream of water or air). The pressure rotates the second impeller, thus rotating the shaft and the first impeller.

The coupling section can also contain channels or cavities through which fluid can be circulated to cool or lubricate the components of the coupling section or to introduce drugs, therapeutic agents, diagnostic agents, or other additives into the coupling section. These channels or cavities can also be used for monitoring conditions of the fluid within the coupling and impeller sections (e.g., temperature, pH, $pO_2$, $pCO_2$, electrolyte concentration) or for taking samples of the fluid in the coupling or impeller sections. In some embodiments, fluids can also be commingled with or removed from the fluid being moved by the impeller.

The impeller section can also incorporate an impeller housing that defines a chamber, and an inlet and an outlet through which fluid is pumped.

An alternative embodiment of the invention is also disclosed in which several rotary units, consisting of the internal components of a coupling section, are mounted on a rotating disk such that each rotary unit may be successively moved into coupling alignment with an impeller as the preceding rotary unit wears out. The rotating disk can be rotated manually or by automated means, including a magnet attached to the rotating disk which can be turned by another magnet.

BRIEF DESCRIPTION OF THE FIGURES

FIG. 6 is a fragmentary diagram of several embodiments of a magnetic component of the pump of the instant invention.

FIG. 7 is a cross-sectional diagram of an alternative embodiment of the pump of the instant invention.

FIG. 9 is a fragmentary diagram of an alternative embodiment of the instant invention.

DETAILED DESCRIPTION OF THE INVENTION

Figure 1:
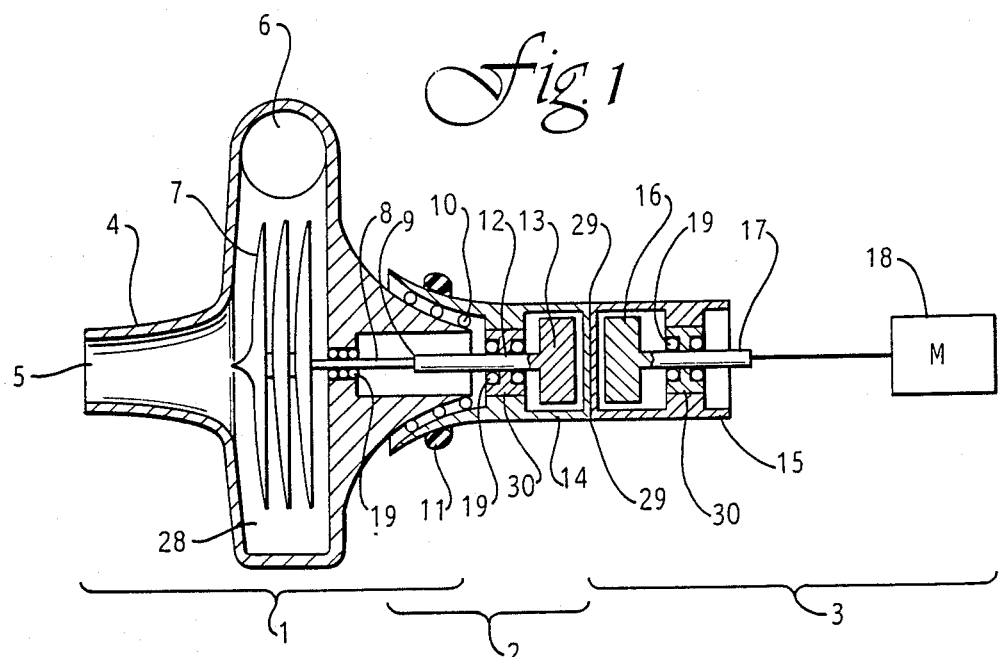
FIG. 1 is a cross-sectional diagram of the preferred embodiment of the pump of the instant invention.

FIG. 1 depicts the preferred embodiment of the pump of the instant invention. The pump is comprised of three sections: the impeller section 1, the coupling section 2 and the driving section 3. The impeller section 1 incorporates an impeller housing 4 that defines a pumping chamber 28 through which fluid is pumped. There is at least one inlet 5 and at least one outlet 6 within the impeller housing 4 through which fluid can enter and exit, respectively. Within the impeller housing 4 is an impeller 7 which is mounted such that it can be rotated when the impeller shaft 8 is rotated. The impeller section 1 can also include seals 19 for preventing fluid from leaving the pumping chamber 28. The impeller section 1 could also incorporate bearings to aid the rotation of the impeller shaft 8, although none are shown in FIG. 1.

The coupling section 2 incorporates a coupling housing 14 in which a coupling shaft 12 is mounted such that it can be rotated. The coupling shaft 12 is connected at one end to a first magnet 13 such that when the first magnet 13 is rotated, the coupling shaft 12 is rotated. The coupling section 2 can also include seals 19 for preventing fluid from entering portions of the coupling section 2 or preventing lubricating or cooling fluid from escaping into the impeller section 1. Rotation of the coupling shaft 12 is assisted by bearings 30, although such assistance is not a required component of a pump of the instant invention.

The drive section 3 incorporates a drive housing 15 in which a drive shaft 17 is rotatably mounted. The drive shaft 17 is attached at one end to a second magnet 16 such that when the drive shaft 17 is rotated, the second magnet 16 is rotated. Rotation of the drive shaft 17 is assisted by bearings 30, although such assistance is not a required component of a pump of the instant invention. The drive section 3 can also include seals 19 to keep lubricating and cooling fluids in their proper place. The drive shaft 17 is connected to a motor 18 that rotates the drive shaft 17.

The impeller section 1 and coupling section 2 are connected such that the impeller shaft 8 can be rotated by the coupling shaft 12. In FIG. 1, the impeller shaft 8 is joined to the coupling shaft 12 at coupling point 9 such that rotation of the coupling shaft 12 rotates the impeller shaft 8 and, as a result, the impeller 7, thus pumping fluid through the pumping chamber 28. The connection of the impeller shaft 8 and the coupling shaft 12 could take any form or configuration by which rotation of the coupling shaft 12 will cause rotation of the impeller shaft 8, including but not limited to connections similar to that of FIG. 1 gear mechanisms, magnetic connections (for example, that shown in FIG. 7 at 35), or electrical conduction or induction. Incorporation of some of these mechanisms into the impeller section 1 would negate in part the advantage of being able to dispose of the impeller section 1 without disposing of other components with continued useful lives or which are expensive to replace; however, such an embodiment would still allow the components, including magnets, to be saved and still provide, at least, that limited advantage over prior devices.

The impeller housing 4 and the coupling housing 14 can be held together by a variety of mechanisms. In FIG. 1, the impeller housing 4 is fitted with a plurality of friction rings 10 that, when pressure is applied to the connection area by a clamping ring 11, the friction rings 10 are pressed against the coupling housing 14 and provide resistance from pulling the housings apart. Conversely, the friction rings 10 could be fitted on the coupling housing 14. The connection point 9 of the impeller shaft 8 and the coupling shaft 12 also help to hold the housings together. Many mechanism whereby the housings can be held together can be used, including those depicted and discused throughout the figures and specification, and will be obvious to those skilled in the art.

In FIG. 1, the coupling housing 14 and drive housing 15 are held together by the magnetic force of the first magnet 13 and second magnet 16. The coupling housing 14 and drive housing 15 can be held together by any means available considering the form of the drive mechanism, including but not limited to the means depicted throughout the figures and specification for connection of the impeller housing 4 and coupling housing 14. Other appropriate means will be obvious to those skilled in the art. The point of junction, at line 29—29, of the coupling housing 14 and the drive housing 15 is impervious to fluid. Although the seals in the impeller housing 4 and the coupling housing 14 could fail, thus exposing the coupling section 2 to fluid, the complete separation of the coupling housing 14 and the drive housing 15 makes exposure of the drive mechanism to fluid impossible, thus extending its useful life. The separation also keeps motor lubricants and detritus away from the fluids circulated throughout the other components of the pump, especially blood. Complete, impervious separation between the coupling housing 14 and the drive housing 15 is desirable although not a required feature of a pump of the instant invention.

Figure 2:
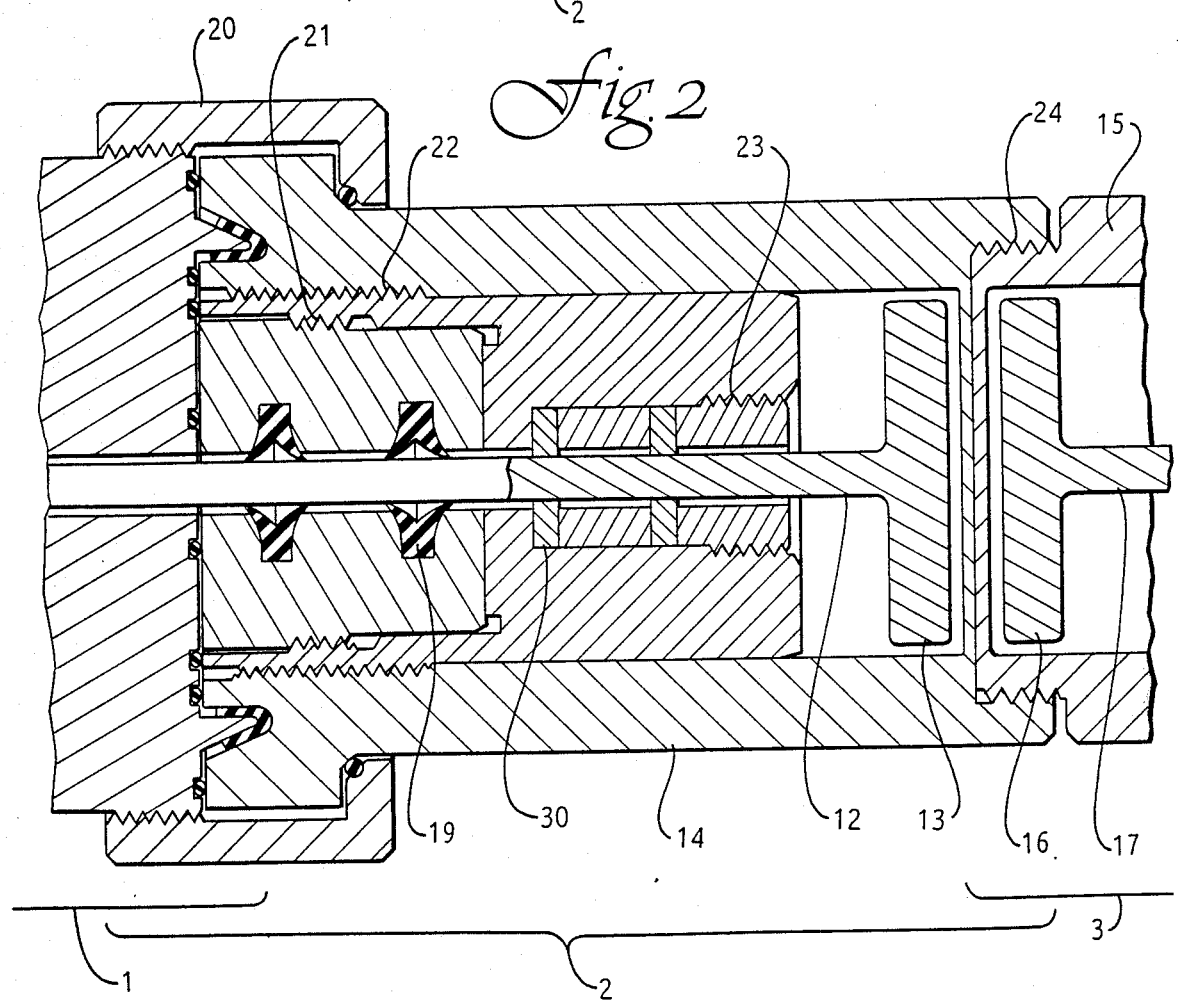
FIG. 2 is an enlarged sectional elevation of the intermediate coupling section of an alternative embodiment of the pump of the instant invention.

FIG. 2 depicts an expanded view of an alternative embodiment of a pump of the instant invention. The coupling section 2 is attached to the impeller section 1 by a threaded clamp 20. FIG. 2 also depicts means whereby various components, including seals 19 and bearings 30, may be removed, replaced and/or services by unscrewing them at 21, 22 and 23. FIG. 2 also depicts a threaded connection 24 between the coupling housing 14 and the drive housing 15. The threaded connections allow construction of "custom-made" coupling sections by removing a given component and replacing it with a component having the desired characteristics. Components within the coupling section that wear out before the others can also be replaced without replacement of the entire section.

Figure 3:
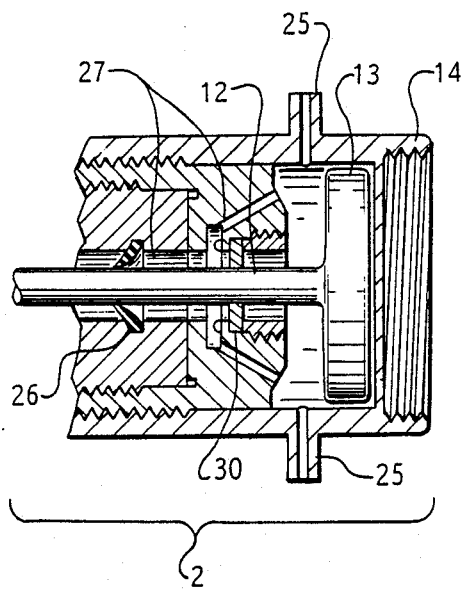
FIGS. 3 through 5 are fragmentary diagrams of the intermediate coupling section of several alternative embodiments of the pump of the instant invention.
Figure 4:
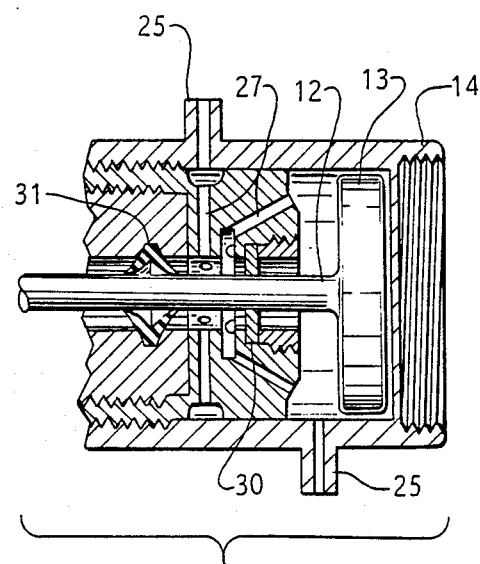
Figure 5:
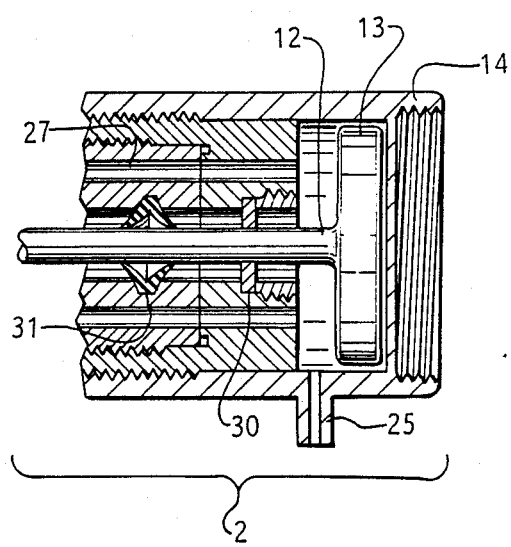

It may be advantageous in some applications to introduce lubricating or cooling fluid into the coupling section 2 of a pump of the instant invention. FIGS. 3 through 5 depict alternative embodiments of the coupling section 2 that provide such a capability. Each embodiment has at least one port 25 through which a coolant/lubricant could be introduced. The coolant/lubricant circulates throughout the cavities within the coupling housing 14 and channels 27 distributed therein depending on the desired route of coolant/lubricant. The coolant/lubricant can be routed along any path of channels 27 within the coupling section 2, including paths bypassing seals and surrounding bearings and seals.. FIG. 3 includes a one-way seal 26 that allows the coolant/lubricant to pass toward the left of the figure, but not the other direction. FIGS. 4 and 5 include impervious seals 31 that prevent coolant/lubricant from moving in either direction. Where the coolant/lubricant should be routed and how channels 27, one-way seals 26 and impervious seals 31 should be arranged within the coupling section to do so will depend on the specific application of the pump and will be obvious to those skilled in the art.

It may be desirable in some applications to circulate fluids other than a coolant/lubricant through the coupling section. "Treating" fluids containing drugs, therapeutic agents, diagnostic agents or other additives could also be circulated from the coupling section 2 into the impeller section 1 if the seal 19 in the impeller section 1 was a one-way seal 25 like that in FIG. 3. In some applications, the one-way seal 25 could be eliminated and fluid could flow freely into and/or out of the impeller section 1 or the flow could be regulated by some mechanism other than a seal. Some "treating" fluids, including saline, could serve as a coolant/lubricant under appropriate conditions and with appropriate design of the pump components. The configuration of ports 25 and channels 27 can also be used to take samples of fluid from within the coupling section 2 that, depending on such configuration, may or may not have been circulated into or removed from the impeller section 1. how to accomplish these ends using an appropriate arrangement of the features described herein and variations thereon which will be obvious to those skilled in the art.

Using known means (e.g., probres, electrodes, syringes), the configuration of channels or cavities and ports can also be used for monitoring conditions of the fluid (e.g., temperature, pH, $pO_2$, $pCO_2$, electrolyte concentration) or for sampling of the fluid Any of the channels or cavities within the coupling section can also, if desired, be fitted with filters to catch particulate matter which may erode from various components of the mechanism.

The ports 25 and channels 27 within the coupling section 2 can be arranged such that fluid can be introduced into, flowed through and/or removed from the coupling section 2. Fluid that is introduced into the coupling section can be, but need not be, temperature controlled and/or filtered by known means before introduction. In some applications, for example as shown in FIGS. 3 and 4, fluid can be removed from the coupling section 2 from one port 25, filtered and/or temperature regulated, and then re-introduced through another port 25. Fluid can also be introduced or removed through a port in the impeller section 1 and then removed or introduced, respectively, from a port 25 in the coupling section. Appropriate arrangement will depend upon the application to which the device is applied and will be obvious to those skilled in the art.

The fluid can be circulated through the coupling section 2 and/or the impeller section 1 by an external source (e.g., a pressure source) and/or by action of the first magnet 13. FIG. 6 depicts several possible forms of the first magnet 13 that will facilitate circulation of fluid throughout the cavities and channels in the coupling section 2. A simple flat-faced magnet 43 will act as a "mono-rotor" and will cause circulation of fluid. The magnet could also be fitted with one or more impellers 44, fins 45 and/or conduits 46 to further assist fluid movement. Appropriate configurations of these and other known means for assisting the fluid circulation in this manner will be obvious to those skilled in the art.

FIG. 7 depicts an alternative embodiment that will allow automated or convenient manual replacement of the rotational elements of the coupling section while the section is being used with an impeller section of extended useful life. In FIG. 7, the coupling section 2 incorporates several "rotary units" comprising a coupling shaft 12 and a first magnet 13.

Although not depicted as such in FIG. 7, each rotary unit could incorporate any of the features of a coupling section described herein, including but not limited to channels for circulation of fluids. Ports 25 extending from a certain embodiment of a coupling section 2, as depicted in FIG. 3 for example, could extend outside the priming chamber 42 when the section is used as a rotary unit. Alternatively, as the rotary unit is aligned with the impeller shaft as described below, the ports 25 could become engaged with means that connect said ports 25 to the outside of the priming chamber 42. Access to the outside of the priming chamber 42 allows control and manipulation of fluids within the coupling section/rotary unit as described above.

Each rotary unit is mounted circumferentially around a rotating disk 33 by a bracket 35 or other fastening mechanism. Alternatively, each rotary unit can be integrally joined directly to or manufactured as a part of the rotating disk 33. Each rotary unit should be, although it need not be, readily removable from the bracket 35 to allow easy replacement with a new rotary unit. The rotating disk 33 is connected to a disk shaft 36 which is in turn connected to a disk rotation mechanism 37. Although a drive housing is not shown in FIG. 7, the first magnet 13 is magnetically coupled to a second magnet 16 and can be rotated as previously discussed. The coupling shaft 12 and impeller shaft 8 are joined at a magnetic connection 32 such that rotation of the coupling shaft 12 rotates the impeller shaft 8. The magnets of the magnetic connection 32 can take any shape that will deter slipping of the magnetic connection 32 during rotation. This type of connection could also be used at the coupling point 9 between the impeller shaft 8 and the coupling shaft 12 in an embodiment similar to that shown in FIG. 1. Moreover, the connection between the impeller shaft 8 and the coupling shaft 12 need not be magnetic. The connection could be made by any means that would allow disengagement, realignment and re-engagement of the connection as described below. Appropriate connection elements and shapes will be obvious to those skilled in the art.

The embodiment of FIG. 7 is most useful where the impeller section 1 of the pump will be used for a period of time longer than the useful life of the rotational components of the coupling section 2 such as in a pump for assisting a patient's cardiac output. As the rotary unit coupled to the impeller shaft 8 is about to wear out a new rotary unit can be rotated into position for engagement with the impeller shaft 8. The coupling housing 14 is fitted with a resilient coupling 34, which can be made of any material or of any form that allows a portion of the coupling housing 14 to be drawn back such that the magnetic connection 32 becomes separated. For example, the resilient coupling 34 could be a rubber accordion-like baffle that could be stretched and flexed. The impeller shaft 8 is fitted with a shaft node 39 such that, as the portion of the coupling section 2 is drawn back, the shaft node 39 contacts a restraining node 40, pulling the magnetic connection 32 apart. The rotating disk 33 is then turned by the disk rotation mechanism 37 such that the next rotary unit revolves into alignment with the impeller shaft 8. The coupling housing 14 is then returned to its original position such that the shaft node 39 contacts the seal 26, thus re-engaging the magnetic connection 32.

The disk rotation mechanism 37 can be a manual or automated system. Preferably, the disk rotation mechanism 37 would incorporate a timer programmed to change rotary units at a prescribed interval. Alternatively, the disk rotation mechanism 37 could be a simple handle that could be pulled and turned manually. Any mechanism that allows the rotary units to be changed at an appropriate time can be used. Other appropriate mechanisms should be obvious to those skilled in the art.

FIG. 7 also depicts a priming chamber 42 in the coupling section 2. Saline, water or other fluid could be introduced into either priming port 41 to fill the priming chamber 42. Similarly, fluids could be removed through the priming ports 41 for analysis or other purposes. A one-way seal 26, or other appropriate structure, could allow "treating" fluids to be pumped into the pumping chamber 28, if desired. Although the priming chamber 42 and priming ports 41 may be desirable in some applications, they are not an essential feature of this embodiment of the instant invention.

Figure 8:
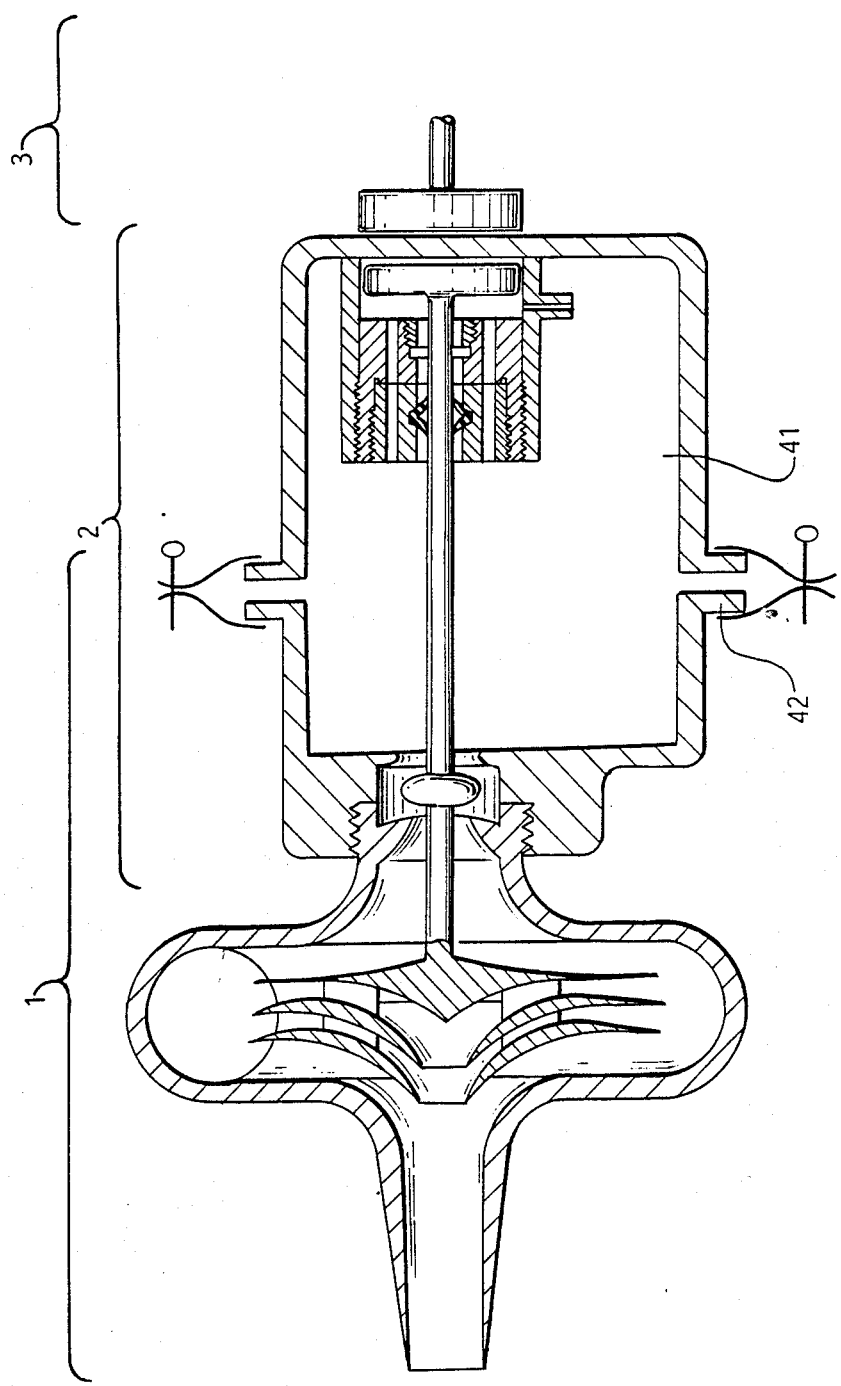
FIG. 8 is a cross-sectional diagram of an alternative embodiment of the pump of the instant invention.

The concept of a priming chamber can also be incorporated in embodiments that do not incorporate the rotational replacement feature depicted in FIG. 7. A coupling section 2 alone could, for example, be contained within a priming chamber 42 as shown in FIG. 8. This would afford all of the advantages and uses of the priming chamber discussed in relation to the embodiment depicted in FIG. 7. The impeller section could be, although it need not be, directly connected to the priming chamber as shown in FIG. 8.

The impeller 7 in a pump of the instant invention can be any mechanism or member, or of any configuration, that will move fluid through the pumping chamber 28. Although the impellers of the type disclosed in U.S. Pat. Nos. 3,647,324 and 4,037,984 are the preferred embodiment, they are not essential to the instant invention. Numerous appropriate impeller designs for a given application will be obvious to those skilled in the art and are intended to be encompassed within that term as it is used throughout this specification and the appended claims.

The coupling shaft 12 may also take on many configurations not specifically depicted herein. For example, the coupling shaft 12 could be a long, thin, flexible sheath capable of turning and bending in an unlimited number of directions. Any form of the coupling shaft 12 that can be connected to the impeller shaft 8 as previously discussed, and can be coupled by a force to the drive section 3 as previously discussed, is intended to be encompassed within that term as it is used throughout this specification and the appended claims.

Although a first magnet 13 and second magnet 16 have been described as the preferred embodiment of the means by which the driving force of the drive section 3 is converted into rotation of the coupling shaft 12, an magnetic mechanism is not the only suitable means for accomplishing this end. Any driving mechanism that can transfer a force to the coupling section 2 that can then be translated into rotation of the coupling shaft 12 is intended to be encompassed within the term "drive means" or "drive mechanism" as those terms are used in this specification and the appended claims. For example, FIG. 9 depicts an alternative embodiment of a pump of the instant invention in which the driving force of fluid (i.e., liquid or gas) pressure 52 is transferred to a second impeller 53 situated within the coupling housing 14 and connected to the coupling shaft 12. Rotation of the second impeller 53 by the fluid pressure 52 causes rotation of the coupling shaft 12. Although using a fluid-based driving mechanism will expose the driving mechanism to some fluid, the depicted embodiment would still insulate the drive mechanism from the biological or other fluid that passes through the pump. Other alternative, non-magnetic drive mechanisms will be obvious to those skilled in the art.

The preferred application of pumps of the instant invention is in the medical field where contamination and tissue cross-reaction during the pumping of blood and other bodily fluids are major concerns that make an economically disposable impeller assembly desirable. However, devices of the instant invention could be used in any situation or application where an element is to be rotated, like an impeller. The fact that certain components can be selectively replaced or disposed of would be advantageous and a device of the instant invention would provide that ability. A device of the instant invention would have applications in, for example, propulsion of boats, other sea-going vessels and aircraft. The term "impeller" as used throughout this specification and the appended claims is intended to encompass any element that is rotated, especially elements that propel an object through a fluid (i.e., liquid or gas). Use of a device of the instant invention in such applications would provide all the advantages discussed herein.

From the foregoing, it will be obvious to those skilled in the art that various modifications in the above described devices can be made without departing from the spirit and scope of the invention. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced therein.

I claim:
1. A rotary pump comprising:
    a coupling section comprising:
        a coupling housing;
        a rotating disk rotatably mounted within said coupling housing;
    at least one rotary unit mounted to said rotating disk for rotation about an axis spaced from the axis of said rotating disk and for revolution about the axis of said disk;
    an impeller attached to said rotary unit by a releasable connection means such that rotation of said rotary unit causes rotation of said impeller;
    means for rotating said rotating disk so as to revolve said rotary unit and align said rotary unit with said releasable connection of said impeller; and
    drive means connected, by operation of a force, to said rotary unit for causing rotation of said rotary unit.
2. The rotary pump of claim 1 wherein said rotary unit comprises a rotational member.

3. The rotary pump of claim 2 wherein said rotational member and said drive means comprise magnets.

4. The rotary pump of claim 2 wherein said rotational member comprises a shaft mounted in said coupling housing for axial rotation and a magnet connected to said shaft.

5. The rotary pump of claim 1 wherein said rotary unit further comprises:
   at least one channel which a fluid can be introduced into or removed from, said channel being in communication with the exterior of said coupling section.

6. The rotary pump of claim 1 wherein said means for rotating said rotating disk comprises:
   a first magnet attached to said rotating disk;
   a second magnet magnetically connected to said first magnet such that rotation of said second magnet rotates said first magnet and said rotating disk; and
   means for rotating said second magnet.

7. A rotary pump for pumping heat sensitive fluids such as blood of other biological fluids, comprising:
   an impeller housing defining a pumping chamber, said impeller housing including structure defining a fluid inlet and a fluid outlet in fluid communication with said pumping chamber;
   an impeller assembly including a fluid contacting impeller rotatably received within said impeller housing and an elongated impeller shaft having a impeller shaft first portion operably coupled to said impeller for rotation therewith, said impeller shaft extending outwardly from said impeller housing;
   a driving section including a motive means and a driving section magnet drivingly coupled to said motive means for rotation of said driving section magnet by said motive means; and
   a coupling section interposed between said impeller housing and said driving section and detachably coupled to said impeller housing, for operably coupling said motive means to said impeller, said coupling section comprising:
      a plurality of rotary units, each of said rotary units comprising an impeller assembly magnet, a impeller shaft second portion adapted for selective alignment with said impeller shaft first portion and operably coupled to its respective impeller assembly magnet for rotation therewith, an impeller assembly magnet housing for carrying said impeller assembly magnet in magnetically coupled relationship with said driving section magnet;
      a rotating member, rotatably mounted within said coupling section, to which said rotary units are attached and upon which said rotary units are arranged about the circumference of a circle;
      means for rotating said rotating member so as to selectively align said impeller shaft first portion with said impeller shaft second portions within said rotary units such that, upon alignment of a particular rotary unit with said impeller shaft first portion, rotation of said impeller assembly magnet within said particular rotary unit will cause rotation of said impeller shaft first portion.

8. The rotary pump of claim 7 wherein a seal member is carried by said impeller shaft, said seal member comprising a one way seal whereby fluids may be introduced into said pumping chamber from said coupling section through said seal member, and fluids within said pumping chamber are blocked by said seal member from flowing from said pumping chamber through said seal member.

9. The rotary pump of claim 8 wherein said seal member is carried by said impeller housing.

10. The rotary pump of claim 7 wherein said impeller assembly magnet housing includes means for isolating said impeller housing and said impeller assembly from fluid communication with said driving section.

11. The rotary pump of claim 7 wherein said coupling section includes a fluid containing chamber, said impeller shaft and said impeller assembly being received within said fluid containing chamber, said coupling section further including structure defining a fluid inlet port and channel means operably coupled to said inlet port for channeling fluid through said coupling section fluid containing chamber.

12. The rotary pump of claim 11 wherein said coupling section includes structure defining a fluid outlet port operably coupled to said channel means whereby cooling fluid can be introduced into said coupling section fluid containing chamber through said inlet port, circulated through said fluid containing chamber by said channel means, and removed from said fluid containing chamber through said outlet port.

13. The rotary pump of claim 7 wherein said impeller shaft supporting means comprises shaft supporting bearings.

14. The rotary pump of claim 7 wherein said means for rotating said rotating member comprises:
   a first magnet attached to said rotating member;
   a second magnet magnetically coupled to said first magnet such that rotation of said second magnet rotates said first magnet and said rotating member; and
   means for rotating said second magnet.

* * * * *